US011229426B2

(12) United States Patent
Krinninger et al.

(10) Patent No.: US 11,229,426 B2
(45) Date of Patent: Jan. 25, 2022

(54) MEDICAL MECHATRONIC MALE AND FEMALE INTERFACE DEVICE

(71) Applicant: Brainlab Robotics GmbH, Munich (DE)

(72) Inventors: Maximilian Krinninger, Weßling-Oberpfaffenhofen (DE); Stephan Nowatschin, Munich (DE); Christian Kühnau, Munich (DE); Daniel Roppenecker, Munich (DE); Dominik Gierlach, Munich (DE); Johannes Agricola, Munich (DE); Stefan Hofberger, Munich (DE)

(73) Assignee: Brainlab Robotics GmbH, Munich (DE)

( * ) Notice: Subject to any disclaimer, the term of this patent is extended or adjusted under 35 U.S.C. 154(b) by 65 days.

(21) Appl. No.: 16/481,224

(22) PCT Filed: May 14, 2018

(86) PCT No.: PCT/EP2018/062327
§ 371 (c)(1),
(2) Date: Jul. 26, 2019

(87) PCT Pub. No.: WO2018/215223
PCT Pub. Date: Nov. 29, 2018

(65) Prior Publication Data
US 2020/0163658 A1    May 28, 2020

(30) Foreign Application Priority Data
May 23, 2017    (DE) .................... 10 2017 111 302.9

(51) Int. Cl.
*A61B 17/00*    (2006.01)
*A61B 90/50*    (2016.01)
(Continued)

(52) U.S. Cl.
CPC .............. *A61B 17/00* (2013.01); *A61B 90/50* (2016.02); *H01R 33/765* (2013.01); *H01R 33/97* (2013.01);
(Continued)

(58) Field of Classification Search
CPC combination set(s) only.
See application file for complete search history.

(56) References Cited

U.S. PATENT DOCUMENTS 6,116,966 A    9/2000   Little et al.
8,870,141 B2   10/2014  Abri et al.
(Continued)

FOREIGN PATENT DOCUMENTS

CA    2527536 A1   12/2004
DE   19526915 A1    2/1997
(Continued)

*Primary Examiner* — Scott Luan
(74) *Attorney, Agent, or Firm* — BakerHostetler

(57) ABSTRACT

A medical mechatronic male interface device for coupling a surgical assistance system to a mounting structure has a base with an end face, a functional body, extending from the end face, first mechanical coupling means for positive and/or non-positive coupling to a corresponding medical mechatronic female interface device, and at least one first electronic interface for connecting to a corresponding second electronic interface of the female interface device. The functional body has a centring device to center the surgical assistance system free of play relative to the base. The centring device has a first functional surface, a second functional surface, and a third functional surface that are not parallel to each other and that have normals which do not lie in a common plane. A corresponding female interface device and a mounting arm and a surgical assistance system are also described.

9 Claims, 13 Drawing Sheets

(51) Int. Cl.
*H01R 33/76* (2006.01)
*H01R 33/97* (2006.01)
*A61B 34/30* (2016.01)

(52) U.S. Cl.
CPC ........... *A61B 2017/00477* (2013.01); *A61B 2034/301* (2016.02); *H01R 2201/12* (2013.01)

(56) References Cited

U.S. PATENT DOCUMENTS

| | | | |
|---|---|---|---|
| 2004/0242060 | A1 | 12/2004 | Plzak |
| 2005/0238418 | A1 | 10/2005 | Surma et al. |
| 2014/0276951 | A1* | 9/2014 | Hourtash .............. A61B 34/37 606/130 |
| 2015/0150547 | A1 | 6/2015 | Ingmanson et al. |
| 2015/0157320 | A1 | 6/2015 | Zergiebel et al. |
| 2016/0119001 | A1 | 4/2016 | Fonseka et al. |
| 2017/0095300 | A1 | 4/2017 | Devengenzo et al. |
| 2017/0365959 | A1* | 12/2017 | Flechl .................. H01R 13/642 |
| 2018/0071049 | A1 | 3/2018 | Nowatschin et al. |

FOREIGN PATENT DOCUMENTS

| | | |
|---|---|---|
| DE | 102011003036 A1 | 7/2012 |
| DE | 102011004926 A1 | 9/2012 |
| DE | 102014016823 A1 | 5/2016 |
| DE | 102014016824 A1 | 5/2016 |
| DE | 102014019752 A1 | 5/2016 |
| DE | 102015104810 A1 | 9/2016 |
| EP | 1958587 A1 | 8/2008 |
| EP | 3130305 A1 | 2/2017 |
| JP | 6272083 U | 5/1987 |
| JP | 62114290 U | 7/1987 |
| JP | 11339875 A | 12/1999 |
| JP | 2001087971 A | 4/2001 |
| JP | 2015107327 A | 6/2015 |
| JP | 2015112485 A | 6/2015 |
| WO | 2016119001 A1 | 8/2016 |
| WO | 2017025607 A1 | 2/2017 |

* cited by examiner

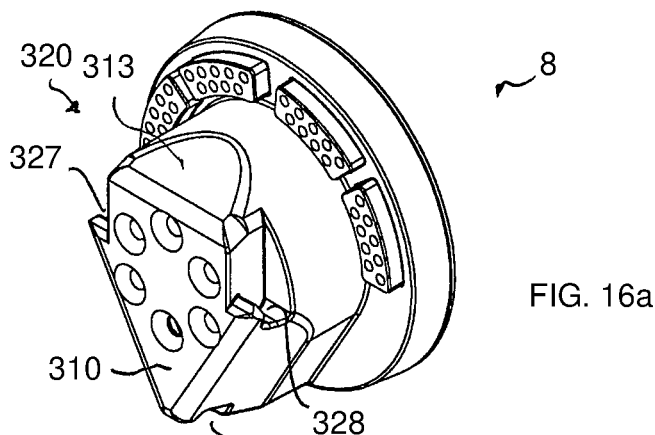
FIG. 16a
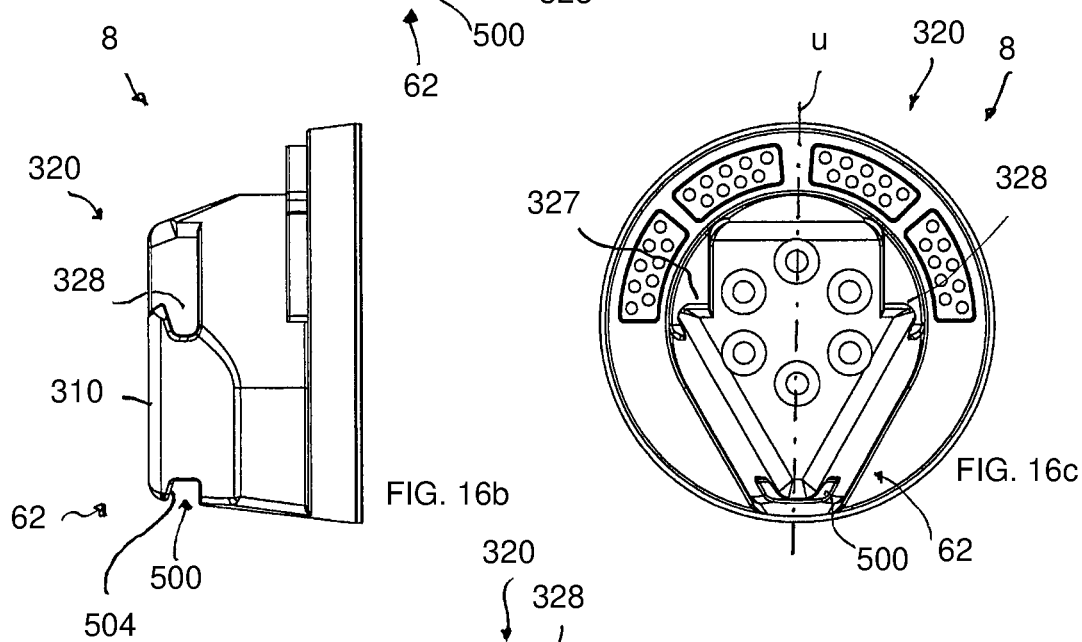
FIG. 16b
FIG. 16c
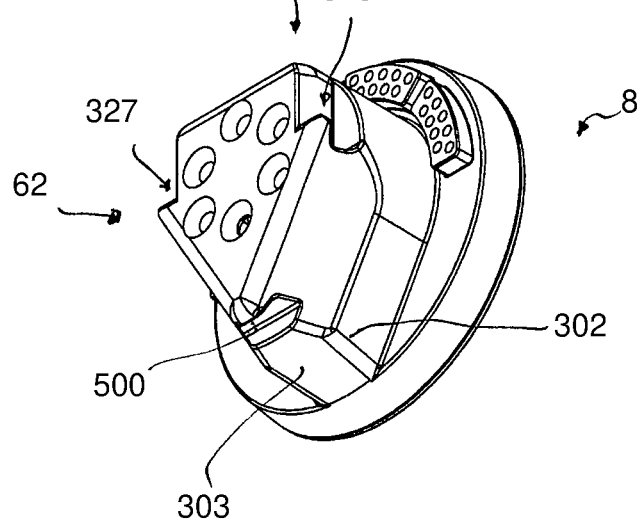
FIG. 16d

Section A-A

MEDICAL MECHATRONIC MALE AND FEMALE INTERFACE DEVICE

CROSS-REFERENCE TO RELATED APPLICATIONS

This application is a National Stage of International Patent App. No. PCT/EP2018/062327, filed on May 14, 2018, which claims priority to German Patent App. No. DE 10-2017-111-302.9, filed on May 23, 2017, the disclosures of which are incorporated by reference in their entirety.

FIELD OF THE INVENTION

The invention relates to a medical mechatronic male interface device for coupling a surgical assistance system to a mounting structure, having a base which comprises an end face, wherein a functional body extends from the end face. The invention further relates to a corresponding medical female interface device for coupling to the male interface device. The invention also relates to a medical mounting arm for mounting a surgical assistance system having a proximal end for attaching the mounting arm to a base and a distal end for receiving the surgical assistance system, two or more arm segments, and two or more joints by means of which the arm segments are connected to each other in an articulated manner; a first interface at the proximal end for connecting the mounting arm to a power source and to an external control unit for transmitting signals to and from the mounting arm; a second interface at the distal end for coupling the mounting arm to an assistance system for controlling the assistance system; and a transmitting device disposed within the mounting arm and connecting the first interface to the second interface for transmitting power and signals between the interfaces. Furthermore, the invention relates to a surgical assistance system having a medical female interface device and a system having a mounting arm of the aforementioned type and one or more surgical assistance systems of the aforementioned type.

BACKGROUND

Mounting arms of the type indicated above have already been known for a long time and are used in surgery, in particular to relieve user of static effort. Such a mounting arm is used in order to mount a surgical assistance system such as a manipulator, an endoscope, a surgical clamp, and the like. Mountings arms of the above type have proven themselves particularly for mounting endoscopes. For endoscopic surgery, a user typically operates an instrument with both hands while an assistant holds the endoscope in order to make the operating field visible on a screen. Holding the endoscope over a longer period of time is very fatiguing. More mounting arms are used for this reason.

One such mounting arm, for example, is known from DE 195 26 915 B4. The mounting device for medical purposes disclosed there comprises a connecting part and a mount for surgical tools and an arm disposed between the mount and the connecting part. The arm is connected to the mount and the connecting part, or to an adjacent arm, via a joint and coupled to a pneumatically actuated device for selectively fixing and releasing the joints, wherein said device fixes the joints under the action of a mechanical spring exerting a braking force on the joint and wherein the device is pneumatically transferable against the force of said spring into a state releasing the joint. An actuating member is disposed at the mounting element at the proximal end of the arm, by means of which a valve can be opened so that the individual joints of the arm can be adjusted. When the actuating member is released, the valve is closed again, so that the joints are fixed.

A similar mounting arm is disclosed in EP 1 958 587 B1. The mounting arm disclosed there also comprises a plurality of joints and a touch-sensitive sensor is provided for actuating the joints. Said sensor is disposed on the mounting arm adjacent to the medical instrument, so that when grasping the medical instrument, the operator makes contact with the touch-sensitive sensor, whereby the joints of the mounting arm are released.

Both of the above-mentioned mounting arms are so-called passive mounting arms, which comprise only braked joints, but no active drives in the joints. The joints are releasable due to the actuation of the control device and locked when these are released again.

A further such mounting arm is disclosed in DE 10 2011 004 926 A1. The mounting arm comprises a plurality of arm segments and a plurality of joints, by means of which the individual arm segments are coupled together. The mounting arm according to DE 10 2011 004 926 A1 further comprises a first interface at the proximal end in order to couple the mounting arm to a standard rail of an operating table. The first interface is substantially implemented in accordance with a clamp. In addition, the mounting arm comprises an interface at the distal end, which is also implemented as a clamp and serves to receive an endoscope. Although said arm is generally well suited for the mere mounting of endoscopes, there is still a need to make the field of use of such mounting arms more flexible, in particular to adapt it to different tasks. Further, it is desirable to improve the safety of such mounting arms such that a risk of injury to a patient is reduced during an operation using the mounting arm.

A mounting arm having the features of the preamble of claim 1 is further known from DE 10 2014 016 823 of the present applicant.

In such mounting arms, there is a need to be able to connect different assistance systems. In particular, depending on the type of operation or the type of mounting task, it is necessary to be able to connect various such systems. In addition, different manufacturers have different interfaces, and it is preferred that these various assistance systems, such as in particular instruments and the like, are connectable to the mounting arm.

SUMMARY OF THE INVENTION

An object of the present invention is to provide both a medical mechatronic male interface device, and a medical female interface device of the type mentioned above, by which a surgical assistance system can be connected in a simple manner and further to increase the potential applications.

The invention solves the problem with a medical mechatronic male interface device in that it comprises first mechanical coupling means for positive and/or non-positive coupling to a corresponding medical mechatronic female interface device and at least one first electronic interface for connection to a corresponding second electronic interface of the female interface device, wherein the functional body comprises a centring device for centring the surgical assistance system relative to the base free of play, wherein the centring device comprises a first functional surface, a second functional surface and a third functional surface, which are not parallel to each other and the normals of which do not lie in a common plane.

The invention makes use of the fact that an interface device not only has to comprise mechanical coupling means for positive and/or non-positive coupling in order to establish a connection, but in particular that a centring device is preferred so that the corresponding medical mechatronic female interface device can be coupled centred to the male interface device. It is possible to compensate for slight manufacturing inaccuracies and to generate a coupling free of play by centring.

Since the functional surfaces are not parallel to each other and their normals do not lie in a common plane, it is possible to generate a statically determined coupling to the corresponding female interface device. The corresponding female interface device preferably comprises corresponding functional surfaces, or other coupling elements, which come into contact with the first, second, third functional surfaces of the male interface device.

The mounting structure can, in the context of the invention, be any mounting structure on which there may be a need to attach a surgical assistance system, such as a tripod, a ceiling stand, an operating table, a room wall, a mounting arm, a robot, and the like.

Although it is preferred that the male interface device comprises an electronic interface, embodiments without the electronic interface are also preferred. In this case, the male interface device is implemented purely mechanically.

The first, second and third functional surfaces jointly define, at least preferably jointly, at least partially, a three-sided pyramid. The arrangement of the normals of the functional surfaces, that is, of the normals which are perpendicular to planes that define the functional surfaces, achieves a pyramidal structure, which preferably tapers away from the base.

Preferably, the functional body is also mirror-symmetrical.

The functional body is preferably mirror-symmetrical in itself. It is preferred in one embodiment that the pyramid is mirror-symmetrical. The plane of symmetry preferably comprises the central axis of the pyramidal structure or the central axis of the functional body and is preferably perpendicular to the base. As a result, the construction can be further simplified and it is possible to use identical parts.

It is further preferred that the functional surfaces are flat. In this respect, it suffices when the functional surfaces are substantially flat, and a slight convexity or concavity is tolerated. So it may be conceivable, for example, that a slightly regular or irregularly curved surface is preferred for reasons of a tensioning of the male and female interface device to each other. However, it is possible to simplify the manufacture by the provision of planar functional surfaces, and a static determination in a coupling to a corresponding female interface device can also be better achieved in this way.

Particularly preferably, the functional surfaces each comprise an angle of 60° to each other. A symmetry of the functional surfaces is achieved as a result. In a further preferred variant, two functional surfaces are implemented identical to each other, but mirror-symmetrical, while the third functional surface is substantially perpendicular to the plane of symmetry.

In this respect, it is also possible that two functional surfaces include an angle less than 60° to each other, for example 45°, and said two functional surfaces then each include a larger angle, namely preferably 67.5°, with the third functional surface.

It is particularly preferred that the functional surfaces are each inclined at least 20° to a central axis of the functional body. That is, the functional surfaces are inclined by at least 20° to the central axis of the pyramidal structure. A smaller inclination, that is, an inclination close to 20° and preferably less than 30°, can lead to a better positioning perpendicular to the central axis. By contrast, larger inclination angles can lead to better positioning in the axial direction. There is a risk that self-locking will occur at angles less than 20°, and thus release of the coupling of the male interface device to the female interface device is no longer readily possible.

According to a further preferred embodiment, it is provided that the functional body comprises an axial end face. In this respect, it is provided that the pyramid or pyramidal structure resembles a truncated pyramid and does not open into an axial tip. An axial tip is not required to generate a coupling between the male interface device and the female interface device. In this embodiment, therefore, the pyramid or pyramidal structure is shortened to a stump and the functional body comprises an axial end face. The axial end face is preferably parallel to the end face of the base and/or perpendicular to the central axis of the pyramid. In other embodiments, it is conceivable that the end face of the functional body is disposed inclined to the central axis.

According to a further preferred embodiment, the first mechanical coupling means comprises at least one first undercut on the functional body. The undercut is preferably implemented by a recess on the functional body and defines a segment engageable from behind. Preferably, a second undercut is implemented on the functional body, which is particularly preferably implemented mirror-symmetrically to the first undercut.

Preferably, the first and second undercuts are radially accessible, so that a corresponding blocking element of second mechanical coupling means can engage in said undercut.

In a further preferred embodiment, the first mechanical coupling means comprises a third undercut on the functional body. A particularly firm securing of the male and female interface device to each other can be achieved using a total of three undercuts. It should be understood that there may also be embodiments in which the first mechanical coupling means comprises only the third undercut, but not the first and second undercuts.

Preferably, the third undercut is implemented substantially opposite to the first and/or second undercut, so that a corresponding protrusion in a direction opposite to the first and/or second undercut direction can engage in the third undercut. If, for example, protrusions for the first and second undercuts engage from above or inclined upwards in the latter, a protrusion provided for the third undercut engages from below into the latter. An unwanted release can be better counteracted by means of opposite directions.

Furthermore, it is preferred that the third undercut is disposed substantially centrally between the first and second undercut with respect to a centre plane, preferably a plane of symmetry, of the functional body. A more even distribution of forces can thereby be achieved.

In a further preferred embodiment, the functional surfaces taper off radially and/or circumferentially into a circumferential surface of a base body of the functional body.

Preferably, a smooth transition, which is kink-free, is provided between the functional surfaces and the circumferential surface of the base body of the functional body.

Cleaning of the interface device can be simplified and hygiene can be improved as a result. A radius in the transition region between the functional surfaces and the circumferential surface is preferably in a range of 1 mm and more, preferably 0.5 mm and more.

The base body of the functional body can basically have any shape, but is preferably not rotationally symmetrical. This makes it possible for the base body to be able to form a part of the mechanical coupling means and to counteract this in particular in a rotation of the female interface device with respect to the male interface device. Preferably, the base body is implemented substantially cylindrical with a radial nose. The base body thus implemented preferably extends axially from the base. A first axial segment of the functional body is preferably free of functional surfaces; the functional surfaces are preferably provided only in a second axial segment of the base body, which is distal from the base. Preferably, the axial length of the second segment is approximately equal to the axial length of the first segment.

Particularly preferably, the functional body is implemented as a single piece. For example, the functional body is milled from a solid material, or produced by deformation methods. This avoids the functional body comprising joints or the like and hygiene can be improved. In the case in which breakthroughs or the like are provided in the functional body, for example, for screws or electrical pneumatic or hydraulic type of connections, or connections for the passage of functional fluids, in particular therapeutic fluids, medicines and the like, said openings or connections are preferably sealed. This is to avoid liquid being able to penetrate from outside the functional body into the interior of the functional body.

In a further preferred embodiment, the electronic interface is implemented on the end face of the base. The female interface device is preferably coupled to the male interface device in the axial direction relative to the functional body and also in the axial direction relative to the base. On the one hand, the functional body is completely available for mechanical coupling and also for transmitting fluids or the like by the electronic interface being implemented on the end face of the base. On the other hand, it is possible for the electronic interface to be equipped with a matching coupling direction, such as the functional body. That is, the electronic interface is also preferably coupled in the axial direction. The electronic interface preferably comprises a plug connection.

Preferably, the electronic interface comprises two or more blocks having electronic contacts. Each block preferably comprises a plurality, two or more electronic contacts. The blocks can be configured redundant, that is, that two or more blocks comprise the same electronic contacts and can thus be used as redundant blocks. However, the blocks can also be assigned differently in other embodiments. It is possible to better shield these multiple blocks from each other by providing multiple blocks. The electrical contacts in turn are preferably insulated and sealed against liquids.

Furthermore, it is preferred that the electronic interface comprises at least two grounding contacts which are disposed such that at least one of said contacts first comes into contact with at least one corresponding grounding contact of the female interface device when coupled to a corresponding female interface device before further electrical contacts are closed. As a result, the electronic interface is grounded before the other contacts are closed. In this way, it is possible and conceivable that the interface devices are coupled and decoupled when voltage is applied, that is, a so-called "hot plug". This is realized, for example, in that the grounding contacts protrude further in the axial direction, so as to achieve the temporal sequence when coupling the interface devices.

According to a second aspect of the invention, the object mentioned above is achieved by a medical female interface device for coupling a surgical assistance system to a mounting structure, wherein the interface device is implemented for coupling to the male interface device according to one of the aforementioned preferred embodiments of the medical mechatronic male interface device, having: a frame defining a central recess for receiving the functional body, second mechanical coupling means for positive and/or non-positive coupling to the first mechanical coupling means of the male interface device, wherein the central recess comprises a centring device for centring the surgical assistance system free of play with respect to the base of the first interface device, wherein the centring device comprises a first functional surface, a second functional surface and a third functional surface, which correspond to the first, second and third functional surfaces of the male interface device for areal contact. It should be understood that the male interface device according to the first aspect of the invention and the female interface device according to the second aspect of the invention comprise the same and similar sub-aspects as set forth in particular in the dependent claims. In this respect, reference is made in full to the above description with regard to the further preferred features, their advantages, and combinations and possible uses. The first, second, third functional surfaces of the female interface device do not necessarily have to be identical to the first, second and third functional surfaces of the male interface device. For example, it is conceivable that the first, second and third functional surfaces of the female interface device are smaller in their areal extent, or comprise a different contour. For example, it is conceivable that the functional surfaces of the female interface device are implemented overall spherical or convex, for example, are formed by three spherical bodies.

The second mechanical coupling means preferably comprises at least a first displaceable bolt for engaging behind the first undercut of the first mechanical coupling means. Preferably, the second mechanical coupling means also comprises a second bolt. The first and/or second bolt preferably protrudes substantially radially into the recess which forms the undercut.

Preferably, the first and preferably also the second bolt are pretensioned in a locking position. The bolt or bolts are preferably displaceable between a locking position and a release position, wherein they engage in the locking position in the undercut or undercuts of the first mechanical coupling means. The pretension in the locking position is preferably released by means of a spring, for example, a spiral spring, a torsion spring, or in a pneumatic manner. It is also conceivable to use a magnetic pretension in order to pretension the bolt or bolts into the locking position.

Particularly preferably, the first bolt is tapered at the free tip. On the one hand, coupling tolerances can be compensated as a result. This preferably also applies to the second bolt. The tapered tip is preferably used to come into contact with a surface of the undercut and that, on the one hand, coupling tolerances can be compensated by the tapering, but also that the female interface device is pulled when bringing the bolt in the locking position against the first interface device due to a wedge effect of the inclined surface of the bolt.

In a preferred embodiment, the second mechanical coupling means further comprises a third displaceable bolt for engaging behind the third undercut of the first mechanical coupling means. If the first mechanical coupling means comprises only the third undercut, the second mechanical coupling means preferably only comprises the third bolt.

It is possible to counteract a rotation about an axis transverse to the central axis particularly effectively by a combination of three bolts.

Preferably, the third bolt is spring-loaded pretensioned and is automatically deflected upon connection of the female interface device to the male interface device and latches into the undercut to counteract a release. The third bolt is preferably implemented as a locking bolt. A release of the third bolt is preferably only possible when first the first and/or second bolts are released.

Furthermore, an actuating device is preferably provided, by means of which the second mechanical coupling means can be offset into a release position. This actuating device preferably comprises a lever pivotally supported on the frame having a gripping segment, the output side being in contact with the first bolt, wherein the first bolt can be brought from the locking position to the release position by actuation of the gripping segment. The actuating device can be manually actuated in this example. It can also be provided that an electronically and/or pneumatically activatable actuating device is provided. This is particularly preferred when the locking device acts magnetically, in particular electromagnetically. Preferably, the actuation is activated by pressing a button or a knob.

In a variant, the third bolt is actuated by means of the actuating device. In another variant, a second actuating device for offsetting the third bolt into a release position is provided independently of the first bolt. Safety can be improved as a result.

In a further preferred embodiment, the first bolt is coupled to the actuating device via at least one film hinge. The bolt is in this embodiment preferably connected as one piece to the actuating device, in particular not reversibly releasable and non-destructive releasable. A film hinge has the advantage that it operates free of play and simultaneously can form a seal. Furthermore, a film hinge, in particular in a manufacture of the male and/or female interface devices, is preferably made at least partially made of plastic.

Furthermore, it is preferred that the second electronic interface is resiliently supported. In turn, coupling tolerances can be compensated as a result. However, it should be understood that it is also possible to resiliently support the first electronic interface.

As described above with respect to the male and female interface devices, the male interface device comprises the first mechanical coupling means and the female interface device comprises the second mechanical coupling means. In preferred embodiments, the male interface device comprises the second mechanical coupling means and the female interface device comprises the first mechanical coupling means. For this case, preferably, the female interface device comprises at least one undercut, and the male interface device preferably comprises at least one bolt which can engage in the undercut. The design of whether the first or second mechanical coupling means are implemented on the male or female interface device depends largely on the purpose and can be chosen freely. A limitation of the invention is not intended herein.

According to a third aspect of the invention, the object mentioned above for a mounting arm of the type mentioned above is achieved in that the second interface of the mounting arm comprises a medical mechatronic male interface device according to one of the aforementioned preferred embodiments of the male interface device according to the first aspect of the invention. Alternatively, the mounting arm comprises the female interface device according to any of the aforementioned preferred embodiments of the female interface device according to the second aspect of the invention. It has been found that it is particularly advantageous to provide the male interface device on the mounting arm. Structural advantages can be achieved as a result and the stability and rigidity can be increased.

According to a fourth aspect, the invention relates to a surgical assistance system having a medical female interface device according to one of the aforementioned preferred embodiments of the female interface device according to the second aspect of the invention. Here too, it is alternatively provided that the surgical assistance system comprises a male interface device.

Furthermore, in a fifth aspect, the invention relates to a system having a mounting arm of the type described above and a surgical assistance system of the type described above, which is coupled to a mounting arm. Preferably, the surgical assistance system is implemented as a robotic manipulator. Preferably, the system comprises two or more surgical assistance systems, of which at least one is implemented using robotics and preferably at least one is implemented passive. A modular system is achieved as a result, and a user can, depending on the task field, couple another surgical assistance system to the mounting arm.

BRIEF DESCRIPTION OF THE DRAWINGS

The invention is explained in more detail by means of embodiments. Shown are:

FIGS. 16*a*-16*d* four views of a second embodiment of the male interface device;

DETAILED DESCRIPTION

Figure 1:
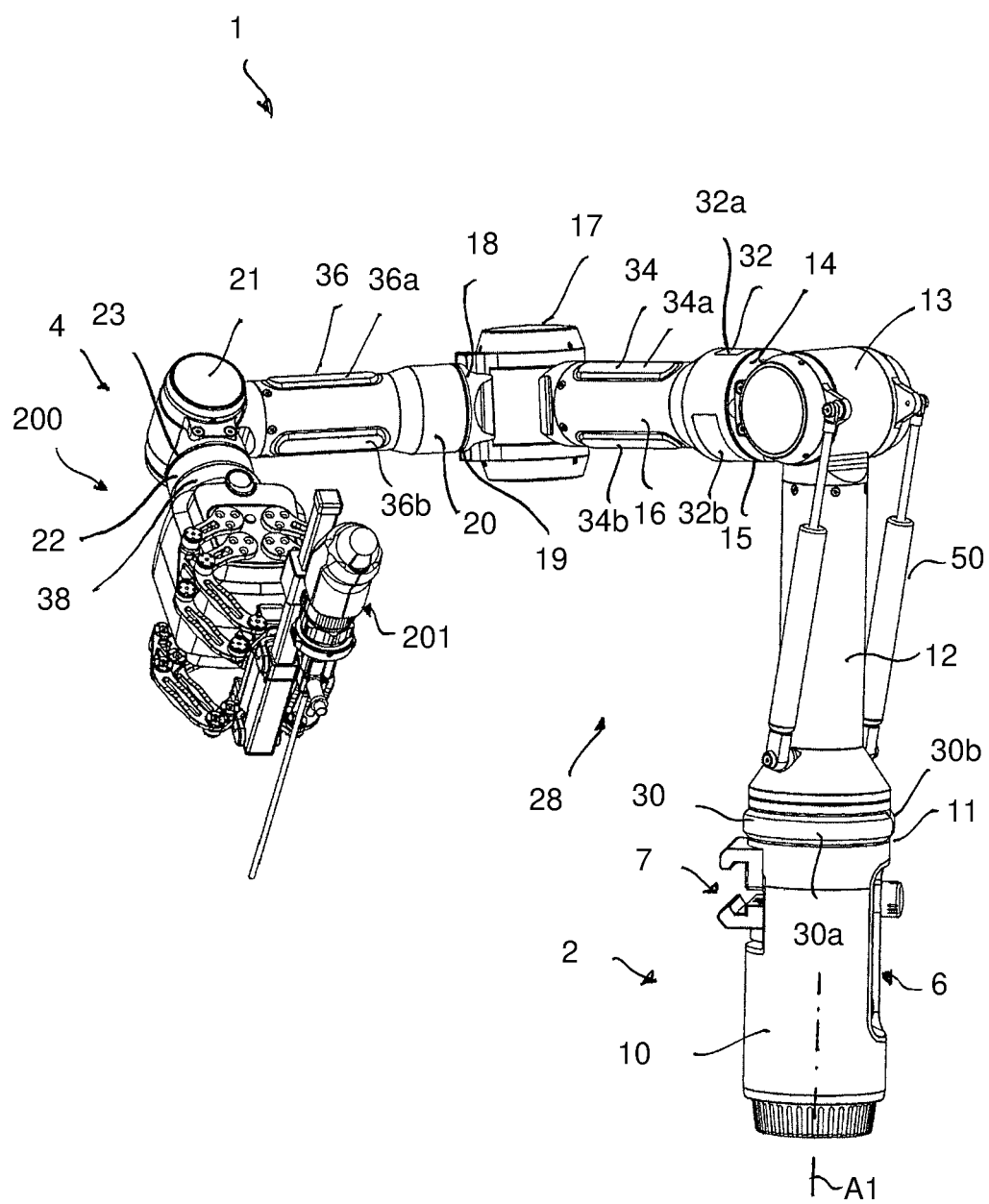
FIG. 1 a perspective view of a mounting arm having a male interface device and a surgical assistance system having a female interface device coupled to each other.

FIG. 1 shows a mounting arm 1 for medical purposes, in particular for mounting a surgical mechatronic assistance system 200 and/or a surgical instrument. The mounting arm 1 comprises a proximal end 2 and a distal end 4. A first interface 6 and a mechanical interface 7 are implemented at the proximal end 2. The interface 7 serves for attaching the mounting arm 1 to a base, particularly to an operating table. The interface 6 serves to transfer energy and to couple the mounting arm 1 to an external control unit. A second interface 8 (cf. FIG. 2) is provided at the distal end 4, via said interface a passive and a mechatronic (active) assistance system, in particular a manipulator device, can be coupled to the mounting arm 1. Preferably, a manipulator device 200 for mounting and manipulating an endoscope 201 is disposed here.

The mounting arm 1 according to FIG. 1 comprises seven arm segments 10, 12, 14, 16, 18, 20, 22, each substantially bar-shaped, and all having substantially identical length except for the last arm segment 22. The seven arm segments 10, 12, 14, 16, 18, 20, 22 are each coupled to each other by means of joints 11, 13, 15, 17, 19, 21, 23, wherein the zeroeth joint 11 couples the mounting arm 1 to the base. The joints 13, 15, 17, 19, 21, 23 are all implemented as rotary joints each having one degree of freedom according to the present embodiment example. According to this embodiment, the zeroeth segment 10 is associated with the zeroeth joint 11, the first joint 13 is associated with the first arm segment 12, the second joint 15 is associated with the second arm segment 14, the third joint 17 is associated with the third arm segment 16, the fourth joint 19 is associated with the fourth arm segment 18, the fifth joint 21 is associated with the fifth arm segment 20, and the sixth joint 23 is associated with the sixth arm segment 22. The joints 11, 13, 15, 17, 19, 21, 23 each comprise pivot axes, wherein adjacent joints each have pivot axes which are perpendicular to each other. Simple positioning of the distal end 4 in space is thereby achieved.

The mounting arm 1 according to FIG. 1 further comprises a control device 28. The mounting arm 1 can be brought into a desired pose, by means of the control device 28, wherein the control device 28 is set up to release the associated joint and/or further joints depending on the configuration and parameterisation of the control device 28 upon contact between an operator and one of the seven arm segments. For this purpose, the control device 28 according to this embodiment comprises five contact segments 30, 32, 34, 36, 38.

Furthermore, according to this embodiment, it is provided that each contact means 30, 32, 34, 36, 38, 40, 42 each comprises two contact element elements 30a, 30b, 32a, 32b, 34a, 34b, 36a, 36b disposed substantially opposite one another. The contact means 30, 32, 34, 36, 38, 40, 42 serve to detect a contact of an operator with the corresponding arm segment 10, 12, 14, 16, 18, 20, 22. When gripping an arm segment 10, 12, 14, 16, 18, 20, 22, the operator comes into contact with both contact means elements 30a, 30b to 36a, 36b, and the associated joint is released only when in contact with both contact means elements 30a, 30b to 36a, 36b of a contact means 30 to 38. That is, when gripping the first arm segment 10 and simultaneously contacting the two contact means elements 32a, 32b, the first joint 11 is released by the control device 28. It is thereby possible that the user can pivot the mounting arm 1 or the arm segments 12 through 22 about the axis A1. When one or both of the two contact means elements 32a, 32b are released, the joint 11 is locked again and pivoting about the axis 1 is no longer possible. For unintentional contact with only one of the two contact means elements 32a, 32b, for example by the user's arm or elbow, the joint 11 is not released and the mounting arm 1 remains in the locked state and holds the pose thereof.

Partially only one contact means for two or more joints is provided in the illustrated embodiments. For example, both the joint 23 and the joint 21 are released upon actuation of the contact means 38.

The control device 28 can for this purpose comprise a controller or microprocessor which is set up to detect a contact between contact means elements 30a, 30b to 42a, 42b and to transmit in electrical signals.

The contact means elements 30a, 30b to 36a, 36b are implemented according to this embodiment as touch-sensitive sensors and detect a pressure of a contact between the operator and the corresponding contact means element 30a, 30b to 36a, 36b. Preferably, the contact means elements 30a, 30b to 36a, 36b are implemented as capacitive touch-sensitive sensors.

In the illustrated mounting arm 1, it is also possible for an operator to simultaneously grasp two arm segments, for example, the arm segment 14 and the arm segment 18, thus simultaneously contacting the contact means elements 34a, 34b and 38a, 38b. The joints 15 and 19 are consequently released, and a pivoting is possible. With this simultaneous release, it is possible to maintain an angular orientation of the arm segments 18 and 20 in space, while only the arm segments 34, 36 are pivoted. A translational movement of the distal end 4 is thus possible. In a preferred embodiment of the mounting arm, in the simultaneous contacting of two arm segments, according to this example of the arm segments 14 and 18, the joints 15 and 19 are not released, but rather all joints lying between said arm segments 14 and 18, that is, according to this embodiment, the joints 17 and 19. The joint 15 remains locked. This is a particularly intuitive operation of the mounting arm. Accordingly, for example, with the contact between operator and the mounting arm segments 12 and 20, the joints 15, 17, 19 and 21 are released.

It can also be seen in FIG. 1 that the mounting arm 1 has a weight compensating device. The weight compensating device 50 according to the present embodiment example comprises a gas pressure spring element coupled to the arm segment 14 and the arm segment 12. Alternatively, the weight compensating device can also comprise a cable pull and/or a balanced counterweight. For the mounting arm 1 according to FIG. 1, the greatest torque acts on joint 15 about the rotary axis A2 thereof. It is therefore preferable to support said joint 15 in particular by means of the weight compensating device 50. When the joint 15 is released by contacting the arm segment 14, a weight acting on the arm segment 14 due to the further arm segments 16, 18, 20, 22 and a manipulator disposed at the interface 8 are supported by the weight compensating device 50, so that the distal end 4 does not immediately "droop" when the segment 14 is grasped.

The basic construction of such a mounting arm is described, for example, in DE 10 2014 016 824 A1, DE 10 2014 019 752 A1 and also in DE 10 2015 104 810 A1. Full reference is made to these documents and their content incorporated by reference herein.

Figure 2:
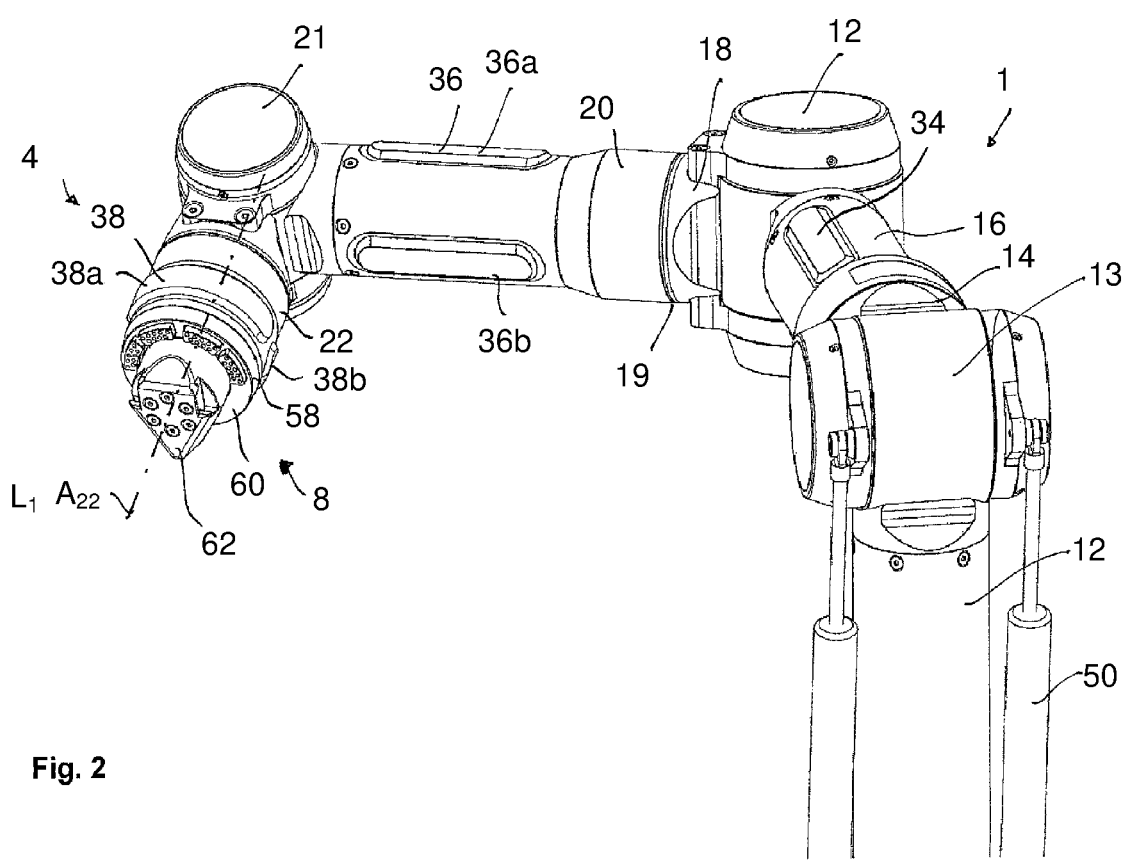
FIG. 2 a detail view of a mounting arm having a male interface device.

The medical mechatronic male interface device 8 according to the invention is provided at the distal end 4 (FIG. 2). This is explained in detail with reference to FIGS. 3 to 6. As can be seen in FIG. 2, the central axis L of the male interface device 8 is coaxial with the axis A22 of the last arm segment 22 forming the distal end 4 of the mounting arm 1.

The medical mechatronic male interface device 8 comprises a base 58, via which the interface device 8 is attached to the last arm segment 22. The base 58 has an end face 60 from which extends a functional body 62, the central axis of which is the axis L. In other embodiments, the interface device 8 may also be attached to any other mounting structure, such as a tripod, a robotic arm, a surgical instrument, an operating table, a ceiling mount, or any other mount or the like.

In this embodiment, the base 58 has an approximately disk-shaped structure and is formed substantially cylindrical in itself. However, the base 58 may also have any other shape and in particular serves to form a connection to the mounting structure. In this respect, it makes sense when the base 58 has a circumferential contour 59 which corresponds approximately to that of the corresponding assembly segment of the mounting structure, as here in particular the circumferential structure of the last arm segment 22. A smooth transition between the base 58 and the last arm segment 22 is thus created. For example, should the last arm segment 22 have an oval structure, it would be preferable for the base 58 to also have an oval circumference 59. In this way, the structure of the functional body 62 can be created independently of the structure of the base 58.

In this embodiment, the functional body 62 extends perpendicularly and axially from the base 58 or the end face 60. The functional body 62 has a base body 300. The base body 300 is in principle cylindrical along the longitudinal axis L, but comprises a radially extending nose 302. The cylindrical segment 304 passes smoothly into the nose 302, which terminates tangentially with its sides 305, 306 (cf. also FIG. 4) to the cylindrical segment 304 of the base body 300. The cylindrical segment 304 extends circumferentially about 180°, preferably about 200°, about the longitudinal axis L.

The functional body 62 also comprises an end face 310, which in this embodiment is aligned substantially perpendicular to the longitudinal axis L. A first functional surface 311, a second functional surface 312 and a third functional surface 313 run at an angle to the longitudinal axis L and at an angle to each other. The first, second and third functional surfaces 311, 312, 313 are planar in themselves, but in each case angled relative to each other and angled relative to the central axis L. The functional surfaces 311, 312, 313 each include an angle α with respect to a plane perpendicular to the central axis L (cf. FIG. 4, the angle α is plotted between the first functional surface 311 and the third functional surface 313 only by way of example), which angle lies in a range of about 60°. The angle α between the further functional surfaces, namely the angle between the second functional surface 312 and the third functional surface 313 and the first functional surface 311 and the second functional surface 312 is identical to the angle α.

Figure 5:
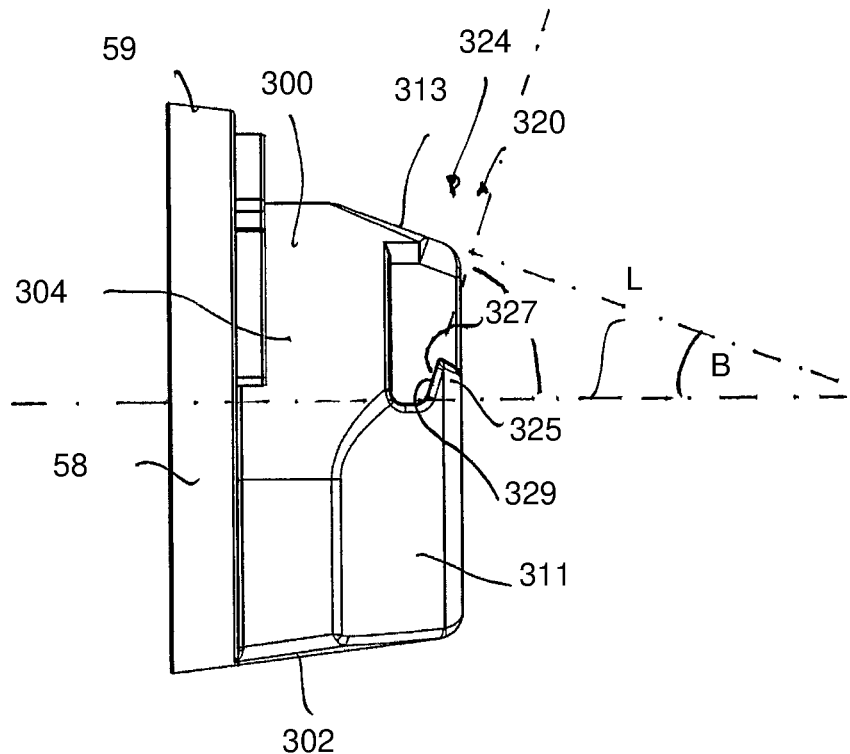
FIG. 5 a side view of the interface device from FIG. 4.
Figure 6:
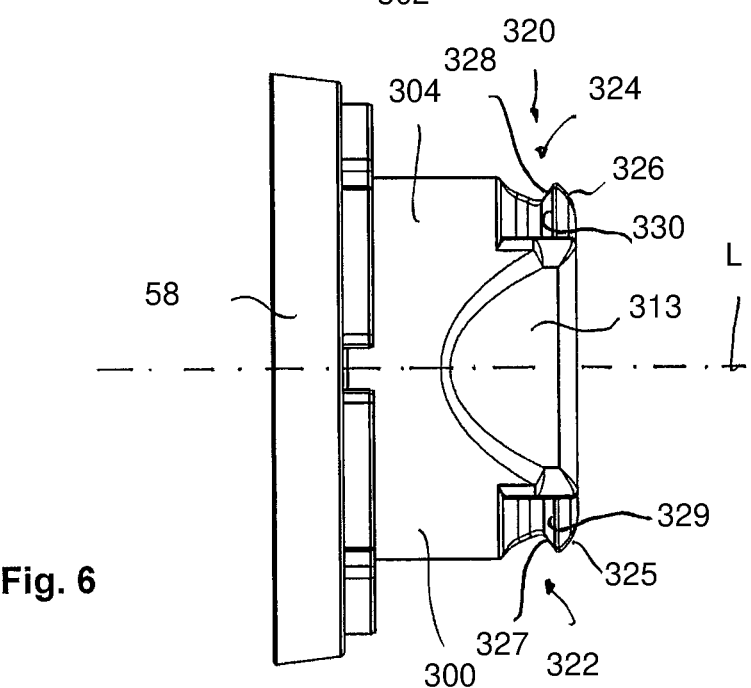
FIG. 6 a top view of the interface device from FIG. 5.

Furthermore, the first, second and third functional surfaces 311, 312, 313 are inclined to the central axis L (cf. FIG. 5). In FIG. 5, only the inclination of the third functional surface 313 to the central axis L is marked, which includes an angle β therewith. The inclination of the first functional surfaces 311 and the second functional surface 312 to the central axis L is preferably implemented identical. The third functional surface 313 includes an angle with the central axis L β in a range of at least 20°. In this embodiment, the angle is β in about 30°. The inclination of the first functional surfaces 311 and the second functional surface 312 is implemented identical in this embodiment and is also approximately at 30° with respect to the central axis L.

The first, second and third functional surfaces 311, 312, 313 also passes into the end face 310 substantially flat and kink-free on the one hand and on the other hand into the circumferential surface of the base body 300. In this respect, the first functional surface 311 tapers off on the one hand at a segment 314 in the end face 310 and on a segment 315 in the base body 300. Likewise, the second functional surface 312 tapers off at a segment 316 in the end face 310 and at a segment 317 in the base body 300. The third functional surface 313 tapers off in a segment 318 in the end face 310, at a segment 319 in the circumferential surface of the base body 300. Each of the segments 314, 315, 316, 317, 318, 319 comprises a radius that is at least 0.5 mm, preferably at least 1 mm. As a result, smooth transitions are created, whereby on the one hand the risk of injury can be reduced, and the cleaning of the male interface device 8 is simplified.

The male interface device 8 further comprises mechanical coupling means 320 which according to this embodiment comprises a first recess 322 and a second recess 324. The recesses 322, 324 are introduced approximately perpendicular to the central axis L and partially intersect with the first and second functional surfaces 311, 312. They also extend through a part of the end face 310, whereby said end face receives an approximately arrow-shaped contour (see in particular FIGS. 3 and 4).

Each of the recesses 322, 324 is limited to the end face 310 by a shoulder 325, 326, which forms an undercut 327, 328. The inwardly directed flank 329, 330 of the undercut 327, 328 is implemented at an angle relative to the central axis L and forms an angle γ (see FIG. 5). The angle γ is less than 90°, preferably 80°, but preferably greater than 45°. The angle γ forms an insertion bevel for the undercut 327, 328, as will be explained later.

Furthermore, insertion bevels 331, 332, which pass into the third functional surface 313, are provided on the recesses 322, 324. These are explained later in more detail.

Figure 3:
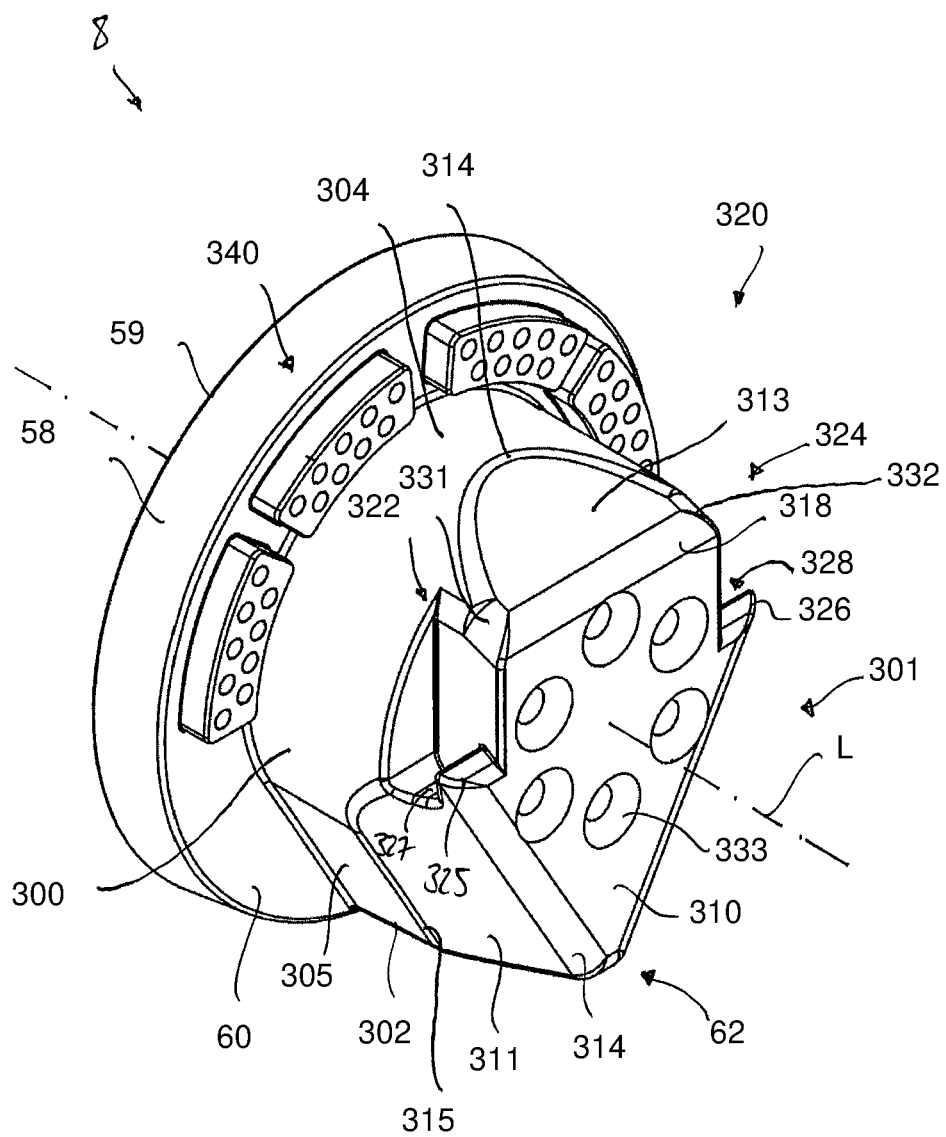
FIG. 3 a perspective view of a medical mechatronic male interface device according to the invention.
Figure 4:
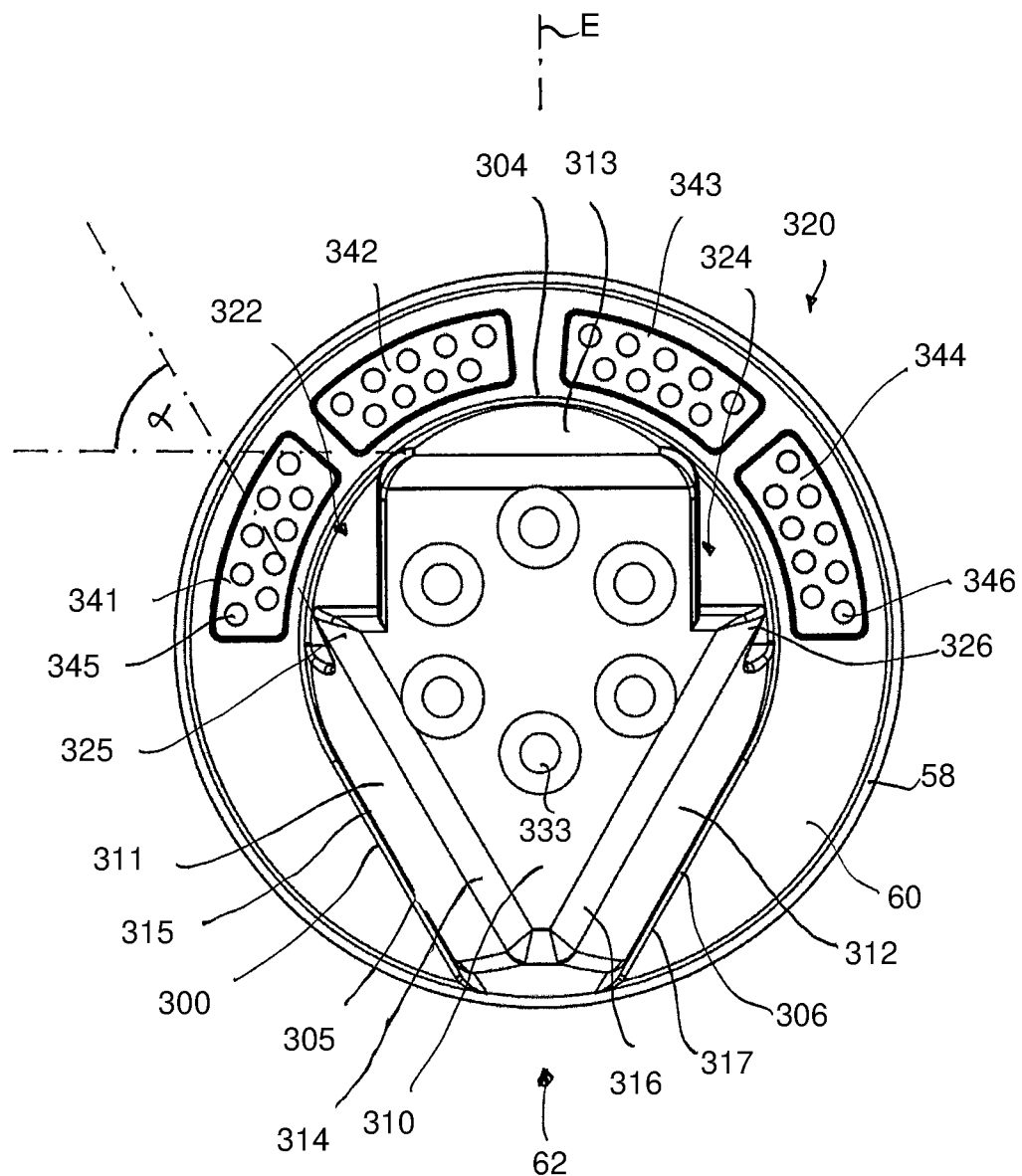
FIG. 4 a frontal view of the interface device according to FIG. 3.

Six holes 33 are further provided in the end face (in FIGS. 3 and 4, only one provided with reference numerals). The male interface device 8 can be connected to a corresponding mounting structure via these holes.

The male interface device 8 also comprises a first electronic interface 340. According to this embodiment, the first electronic interface 340 comprises four blocks 341, 342, 343, 344, each of which comprises a plurality of electrical contacts, in each case nine electrical contacts in this embodiment. The first, second, third and fourth blocks 341, 342, 343, 344 are implemented here as female plugs of the electronic interface 340. They are sealed at their edge opposite the end face 60, but preferably resiliently supported. The plug-in direction and thus the coupling direction of the electronic interface 340 is parallel to the central axis L.

Overall, the male interface device is implemented mirror-symmetrical in its outer structure to the plane E (see FIG. 4). The functional body 62 forms a three-sided truncated pyramid. A particularly simple centring is achieved as a result. The nose 302 of the base body 300 provides an additional protection and securing against rotation relative to the central axis L.

The first electronic interface 340 comprises a first and a second grounding contact 345, 346. The first grounding contact 345 is disposed in the first block 341 and the second grounding contact 346 in a second block 344. The grounding contacts 345, 346 are those contacts which are furthest away from each other. This means that even with a slight tilting of the female interface device relative to the male interface device 8 when coupling always leads to one of the grounding contacts 345, 346 first coming into contact, while only then the remaining electrical contacts of the blocks 341, 342, 343, 344 are closed.

Figure 9:
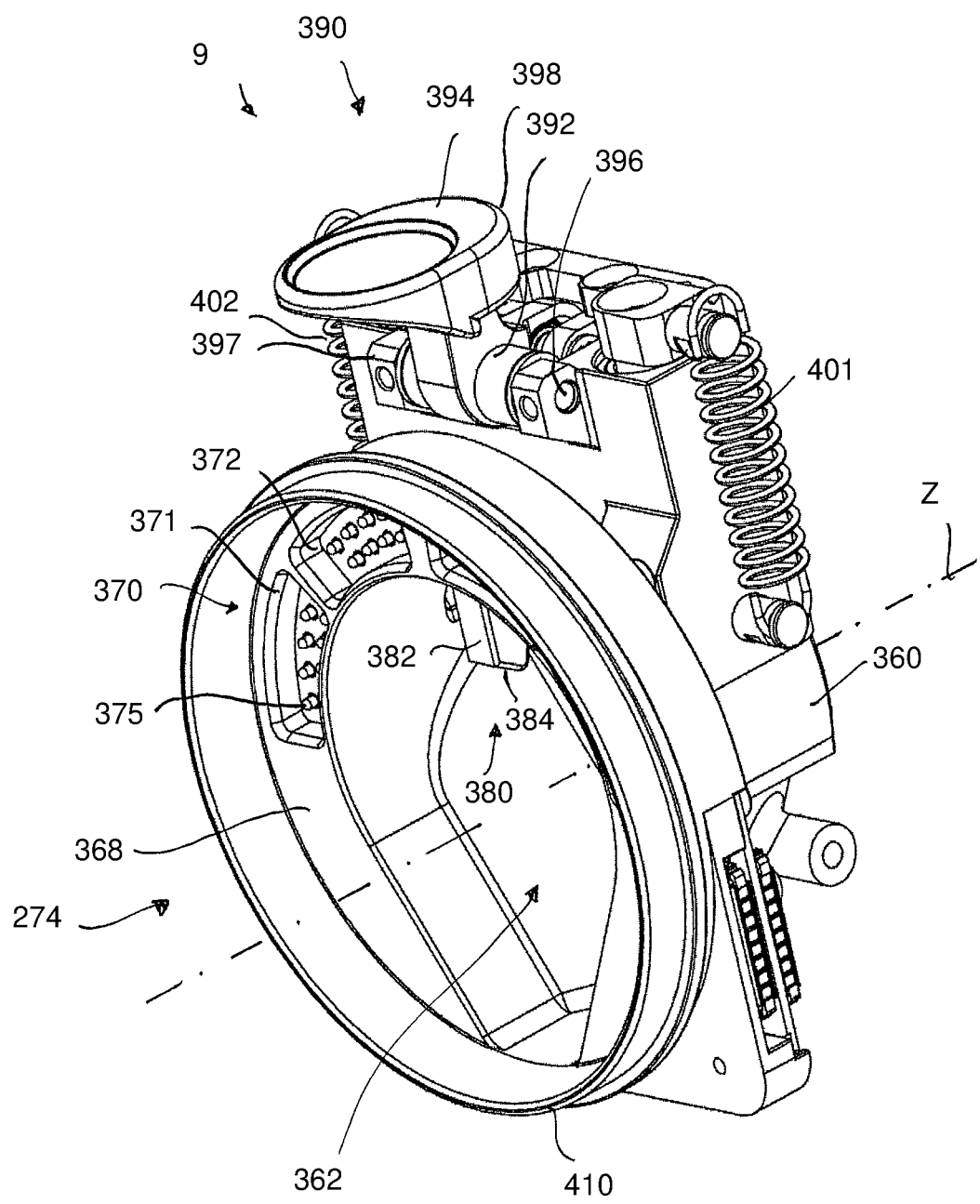
FIG. 9 a perspective view of the medical mechatronic female interface device.
Figure 10:
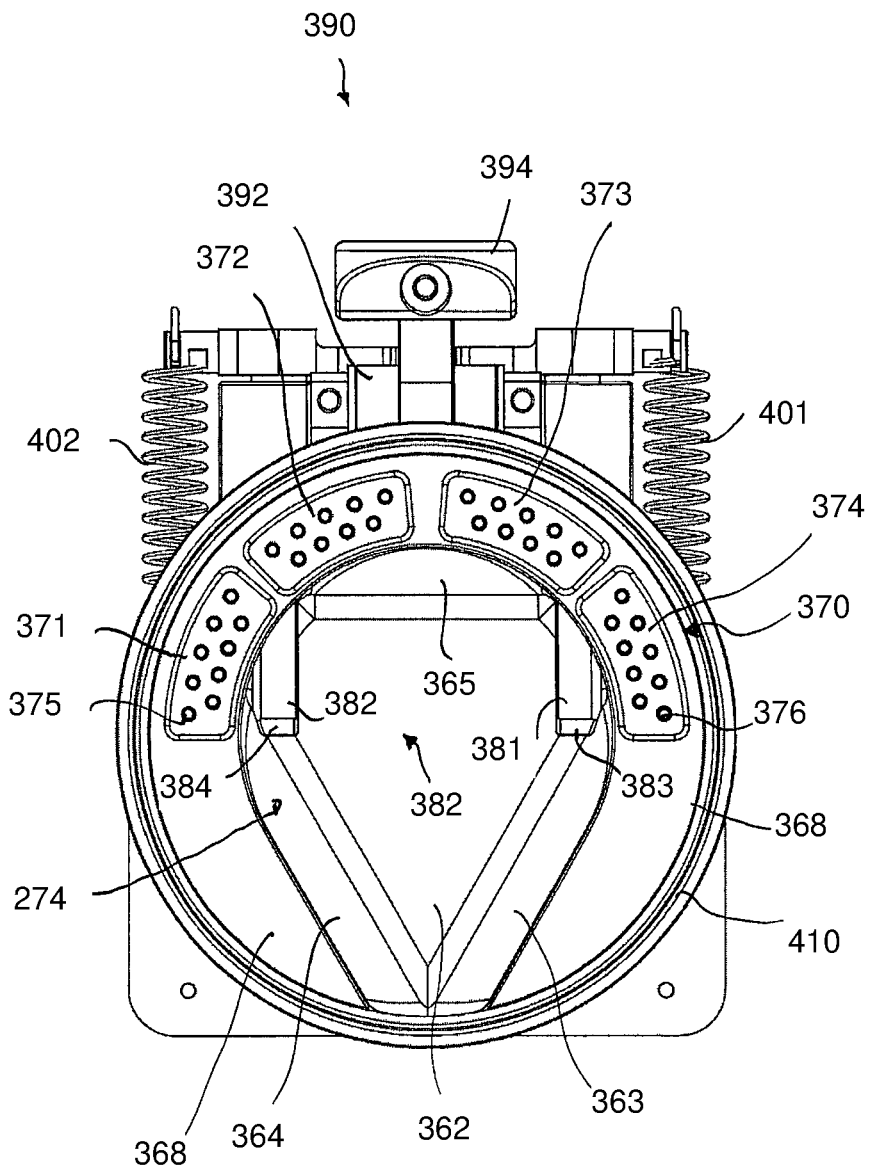
FIG. 10 a frontal view of the interface device from FIG. 9.
Figure 11:
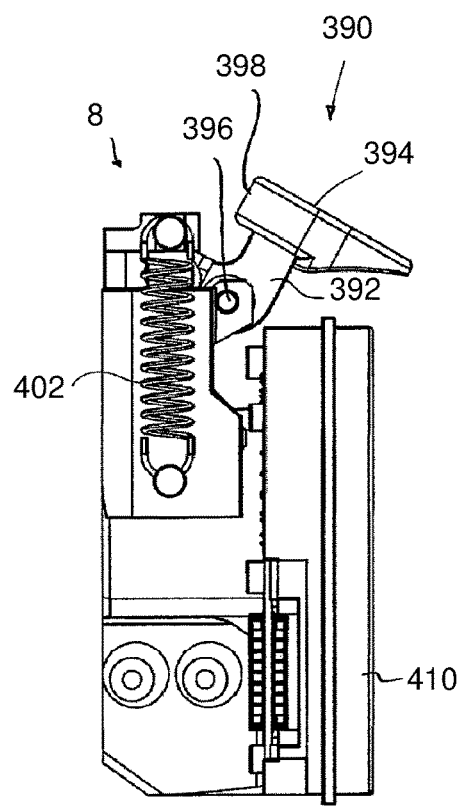
FIG. 11 a side view of the interface device of FIG. 10 having actuated actuating device.

In the following, FIGS. 7 and 8 initially show an overview of the medical female interface device 9, while this will then be described in detail with reference to FIGS. 9 to 11.

Figure 7:
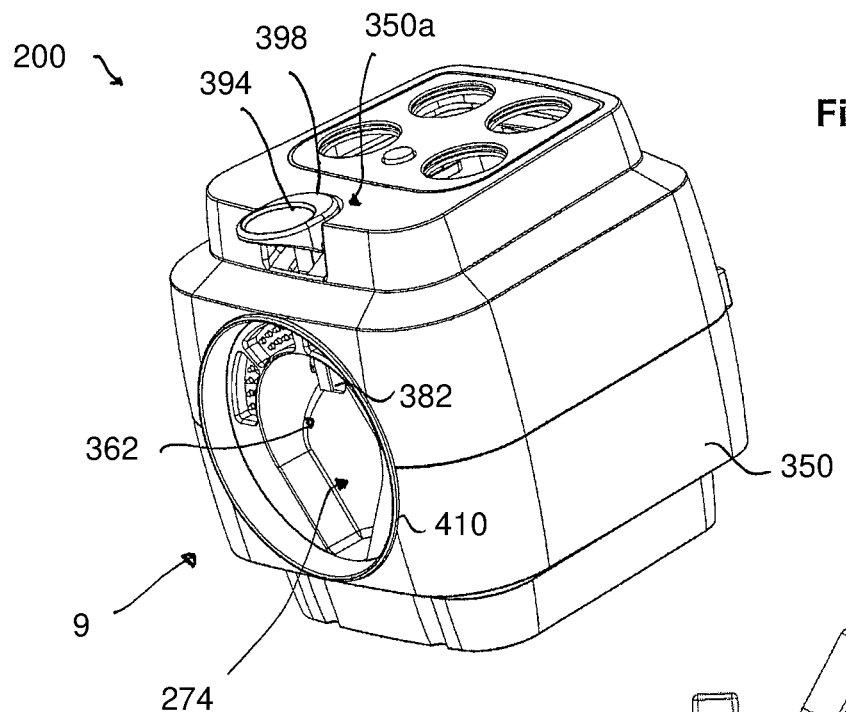
FIG. 7 perspective view of a housing of a surgical assistance system having a female interface device.

In FIG. 7, initially a housing 350 of a surgical assistance system 200, namely a mechatronic manipulator 200, as shown in FIG. 1, is shown in perspective. In the illustration in FIG. 7, all the kinematics have been omitted, but the medical female interface device 9 can be seen on one side of the housing 350.

Figure 8:
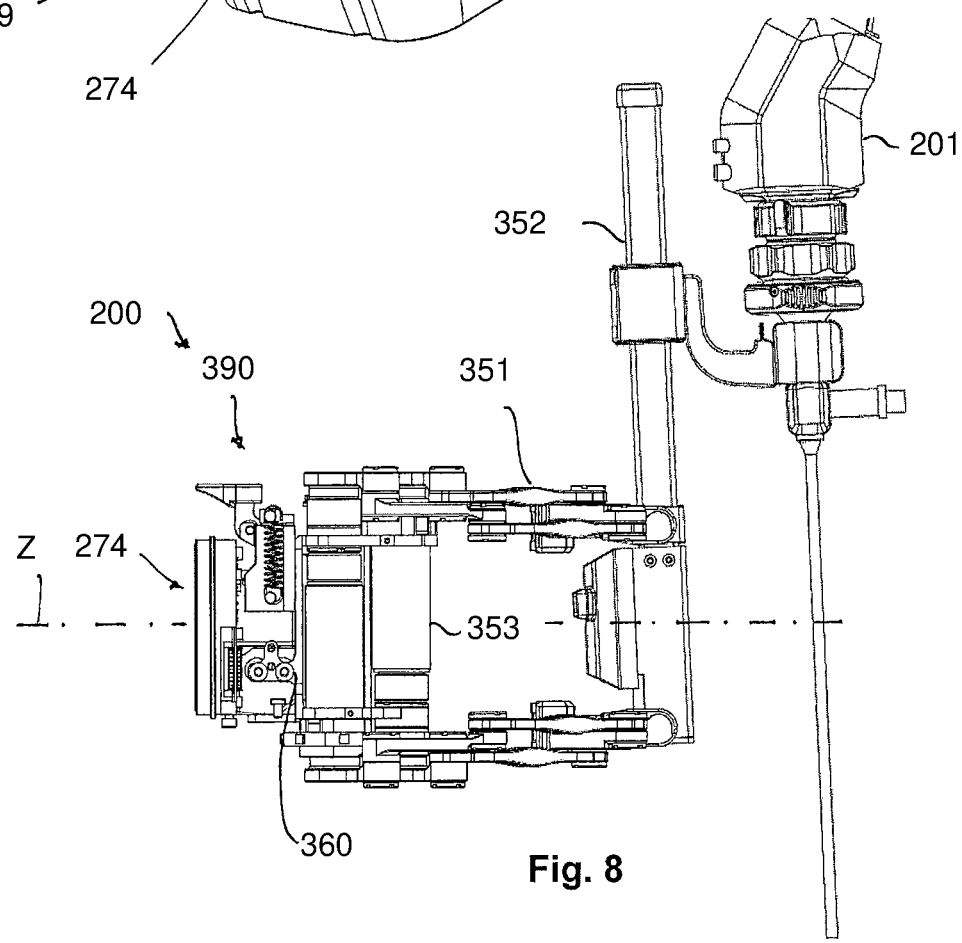
FIG. 8 a side view of a surgical assistance system having the female interface device, wherein the housing is omitted.

In contrast to this, the housing 350 of the surgical assistance system 200, namely the mechatronic manipulator 200, is omitted in FIG. 8, but the kinematics 351 including linear drive 352 and endoscope 201 can be seen. The mechatronic manipulator 200 comprises a drive 353 in the interior, said drive being able to be supplied with control signals and electrical energy via the female interface device 9.

The female interface device 9 for coupling a surgical assistance system to a mounting structure, as in particular the mounting arm 1, is designed for coupling to the male interface device 8, as was explained above with reference to FIGS. 1 to 6. The female interface device 9 comprises a frame 360, which forms a structure for the interface device 9. The interface device 9 further comprises a central recess 274 for receiving the functional body 62, which is implemented in the frame 360. The central recess 274 has a central axis Z, which runs in the coupled state of the female interface device 9 to the male interface device 8 coaxial with the axis L of the male interface device 8. The central recess 274 has a centring device 362, wherein the centring device 362 comprises a female first functional surface 363, a second female functional surface 364, and a third female functional surface 365. These three functional surfaces 363, 364, 365 are best seen in FIG. 10. The functional surfaces 363, 364, 365 are implemented corresponding to the first, second and third functional surfaces 311, 312, 313 of the male interface device 8. In the coupled state, the functional surfaces 363, 364, 365 lie correspondingly against the functional surfaces 311, 312, 313. They therefore also comprise the same inclinations or similar inclinations as the first, second and third functional surfaces 311, 312, 313.

Facing outward, the female interface device 9 comprises an end face 368 which corresponds to the end face 60 of the male interface device 8. A second electronic interface 390 is implemented on the end face 386, said second electronic interface corresponding to the first electronic interface 340. In this embodiment, therefore, the second electronic interface 370 comprises first, second, third and fourth recesses 371, 372, 373, 374, in which a plurality of electrical contacts (not provided with reference numerals) are provided, namely nine electrical contacts, each corresponding to the electrical contacts of the first electronic interface 340. In this respect, the second electronic interface 370 also comprises first and second grounding contacts 375, 376, which correspond to the grounding contacts 345, 346 of the first electronic interface 340. This is achieved in the present case in that the axial length, in the direction of the central axis Z of the grounding contacts 375, 376, is slightly longer than the axial length of the remaining electrical contacts. In this way, it can be ensured that the contact closure between the corresponding grounding contacts 345, 346, 375, 376 takes place first, and only then is the contact of the other contacts closed.

The female interface device 9 additionally comprises second mechanical coupling means 380. The second mechanical coupling means 380 is provided for positive and/or non-positive coupling to the first mechanical coupling means 320 of the male interface device 8. For this purpose, the second mechanical coupling means 380 corresponds to the first mechanical coupling means 320. The second mechanical coupling means 380 in this embodiment comprises a first bolt 381 and a second bolt 382 which extend into the central recess 274 substantially perpendicular to the central axis Z. The first and second bolts 381, 382 are shown in the locked position in FIGS. 7, 9 and 10. The first and second bolts 381, 382 comprise on their end face, that is, at the free axial ends, a chamfer 383, 384. This chamfer 383, 384 corresponds at least in segments to the flank 329, 330 of the undercut 327, 329 of the first mechanical coupling means 320.

Figure 12:
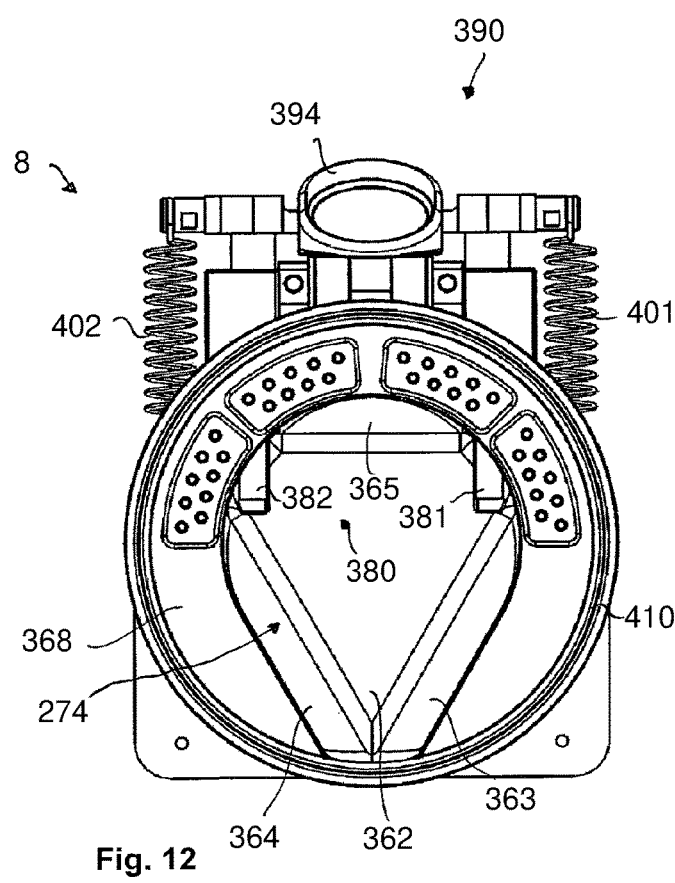
FIG. 12 a frontal view of the interface device from FIG. 11.

The first and second bolts 381, 382 can be brought together from the locking position (FIGS. 7, 9, 10) into a release position (FIGS. 11 and 12) via an actuating device 390.

For this purpose, the first and second bolts 381, 382 are articulated at a common yoke or fork 392, wherein an actuating knob 394 extends from the yoke 392. The actuating knob 394 is connected as one piece to the yoke. The yoke 392 and thus also the actuating knob 394 are pivotally supported about an axis 396 in a support segment 397 of the frame 360. The first and second bolts 381, 382 are raised by pivoting the push button 394 (cf. FIGS. 11 and 12), that is, removed from the central axis Z and at least partially pulled out of the central recess 274, so that in this released state (FIGS. 11, 12), the male interface device 8 with the functional body 92 can be inserted into the central recess 274 of the female interface device 9. That is, the first and second bolts 381, 382 are in any case raised so far that they can pass axially over the protrusions 325, 326. If then the push button 394 is released again, this is brought in the locking position by a spring pretension, which is provided by first and second tension springs 401, 402. That is, the second mechanical coupling means 380 are pretensioned in the locking position. Upon locking, the first and second bolts 381, 382 are inserted from above into the recesses 322, 324 with reference to FIG. 5 and pass behind the undercuts 327, 328. Here, the flanks 329, 330 and the taperings 383, 384 can now be used. If the male and female interfaces 8, 9 are not sufficiently joined, the first and second bolts 381, 382 initially come into contact with their taperings 383, 384 with an upper segment of the protrusions 325, 326, with reference to FIG. 5. The bolts 381, 382 then slide along the inclined flank 329, 330 into the undercut. In this way, it can be ensured that the female interface device 9 can be used on the male interface device 8.

It can be provided that the geometry of the functional surfaces 311, 312, 313, 363, 364, 365 and the positioning of the undercuts 327, 328 and of the first and second bolts 381, 382 is selected such that the first, second bolts 381, 382 always abut the flanks 329, 330, and thus always exert a tensile force on the male and female interface devices 8, 9 in order to achieve a solid coupling. This coupling is then free of play. Due to the static determination of the contacts of the respective functional surfaces 311, 312, 313 and 363, 364, 365, the contact of the functional body 62 with the central recess 274 is also determined statically.

The push button 394 comprises a back 398, which is aligned in the locked position so that it is covered by the segment 350a of the housing 350. If the push button 394 is located in the pivoted position and thus the second mechanical coupling means 380 in the released position, the back 398 is visible. The back 398 preferably comprises a signal colour, for example a red colour. As a result, it is easy for the operator to recognize when the push button 394 is located in the released position (FIG. 11) and thus a secure coupling of the female interface device 9 and the male interface device 8 is not guaranteed.

Other securing units or devices may be provided as an alternative to this optical check by means of the back 398. Thus, for example, it can be provided that by bringing the first and second bolts 381, 382 into the locking position, an electrical contact is closed or opened and, depending thereon, a signal lamp lights up. It is also possible that an acoustic signal is output in a similar manner. Furthermore, it can be provided that at least one of the surfaces 311, 312, 313, 363, 364, 365 is provided one or more pressure sensors which provide a corresponding signal when a threshold is exceeded and/or undershot. For example, if it is determined that a threshold value is undershot, a coupling of the male interface device 8 and the female interface device 9 is not sufficient and a corresponding signal is preferably output. A collar 410 is implemented around the central recess 274 of the female interface device 9. This collar 410 extends substantially axially from the end face 368 and, in the coupled state, surrounds the skin surfaces 359 of the base 358 of the male interface device 8. A further seal is achieved as a result. For this purpose, the collar 410 may be formed, for example, from a flexible material, such as plastic or rubber.

Figure 13:
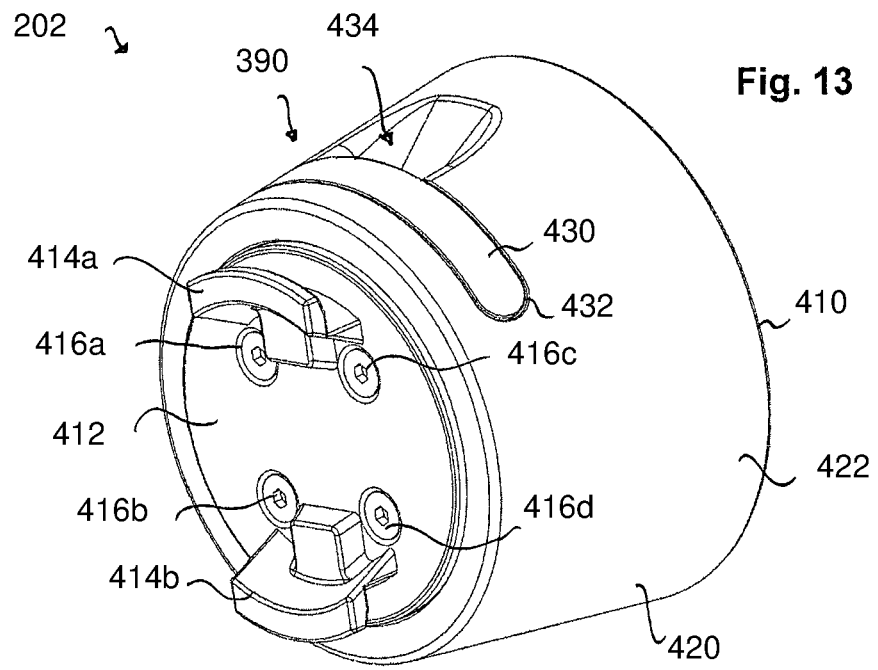
FIG. 13 perspective view of a second embodiment of a surgical assistance system.
Figure 14:
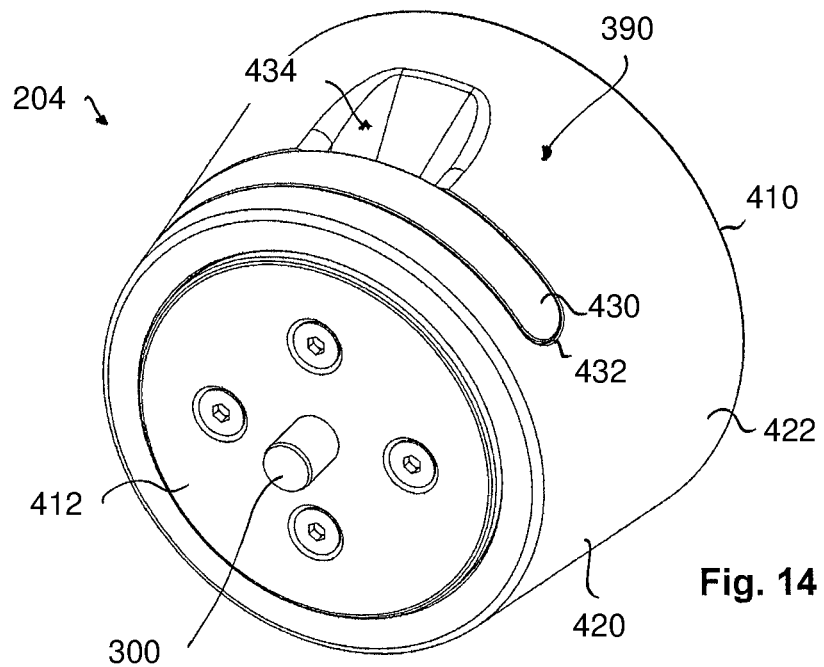
FIG. 14 perspective view of a third embodiment of a surgical assistance system.
Figure 15:
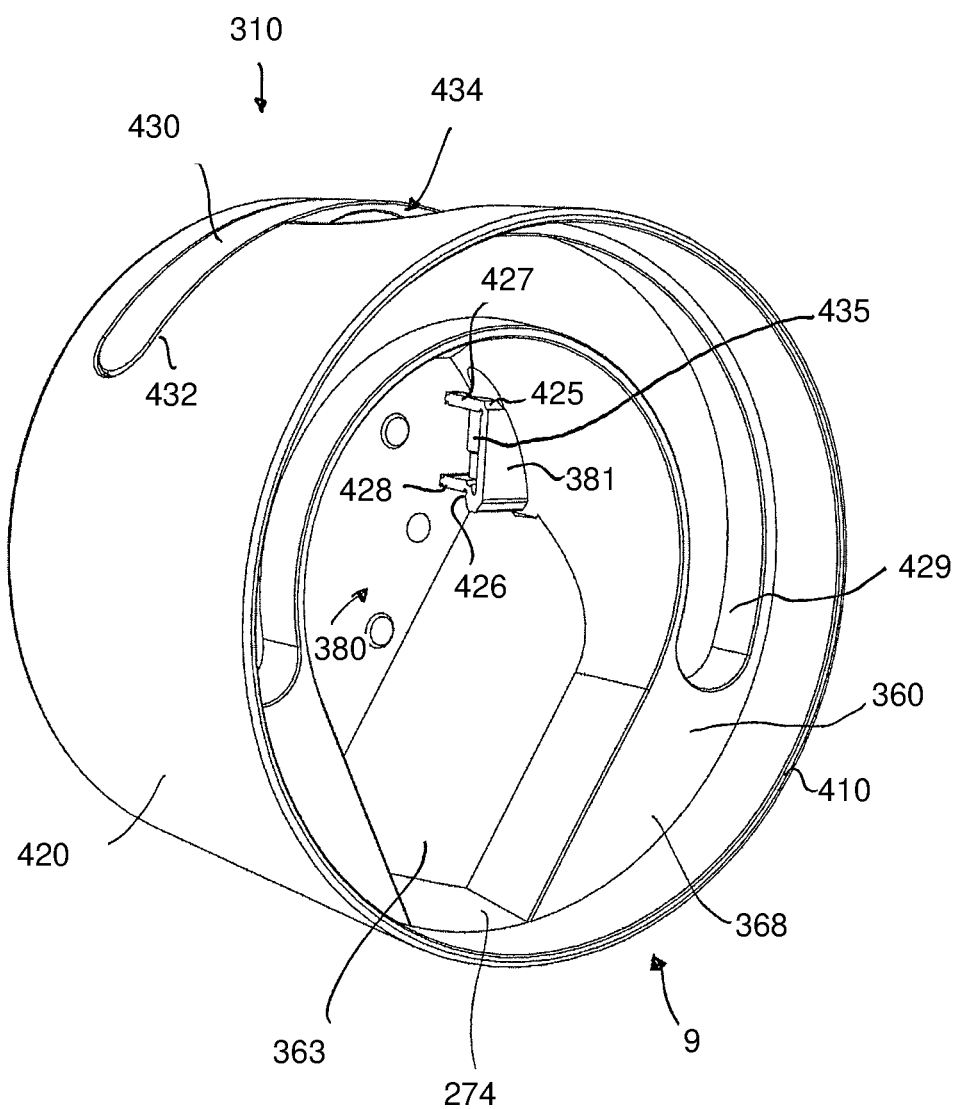
FIG. 15 a rear view of the surgical assistance system from FIG. 13.
Figure 17:
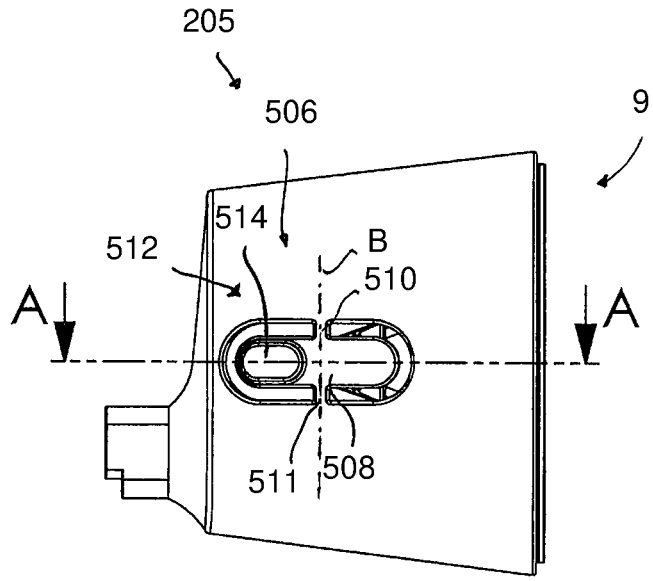
FIG. 17 a side view of a surgical assistance system having a female interface device according to a second embodiment.

FIGS. 13 to 15 now illustrate further embodiments of surgical assistance systems. The same and similar elements of FIGS. 13 to 15 are designated by the same reference numerals as in the previous embodiments and in this respect, reference is made in its entirety.

FIG. 13 shows a surgical assistance system 202 and FIG. 14 shows a surgical assistance system 204. Both surgical assistance systems 202, 204 are implemented here as caps and in this respect passive. The surgical assistance system 202 differs from the surgical assistance system 204 by its front surface 412. From the front surface 412, first and second positive locking elements 414a, 414b, which may serve to receive a medical instrument, extend into the surgical assistance system 202. Such a medical instrument can serve in particular as a coupling piece for an endoscope, a clamp, a laparoscope or the like.

In the embodiment in FIG. 14, the surgical assistance system 204 comprises a threaded shaft 300 instead of the first and second positive locking elements 414a, 414b, which also serves to enable medical instruments to be screwed onto it.

As is also apparent from FIGS. 13 and 14, the end faces 412 are implemented substantially plate-shaped and are screwed by means of four screws 416a, 416b, 416c, 416d to a base body 420 of the surgical assistance system 202, 204. In this respect, 420 different front surfaces 412 can be screwed on the same base body. As a result, a variety of different variants is conceivable. Preferably, for example, standard interfaces for tools, instruments and the like are provided on such front surfaces 412, or manufacturer-specific interfaces for receiving manufacturer-specific instruments.

The base body 420 is formed on its outer surface 422 substantially frusto-conical and comprises the female interface device 9 in its interior. The base body 420 is preferably formed entirely of a plastic.

In contrast to the surgical assistance system 200 of the previous embodiment according to FIGS. 7 to 12, the female interface device 9 according to these two embodiments (FIGS. 13 to 15) does not comprise a second electronic interface device 340, since the surgical assistance systems 202, 204 are implemented passive. Only a single recess 424 is provided in the corresponding segment of the end face 368, to be able to receive the blocks 341, 342, 343, 344 of the male interface device 8.

A further difference from the surgical assistance system 200 is that the first and second bolts 381, 382 (only one is seen in FIG. 15) of the mechanical coupling means 380 are also made of plastic and are connected by means of film hinges 425, 426 to corresponding webs 427, 428, which in turn are hinged to the base body 420. The first and second bolts 381, 382 are pretensioned in the locked position via the film hinges 425, 426. A solid body joint having solid body pretension is thus provided.

A lever 430 is provided to bring the mechanical coupling means 380 according to these second and third embodiments (FIGS. 13 to 15) into the release position, said lever being received substantially flush on a recess 432 of the circumferential surface of the base body 420. The lever 430 can be manually actuated via a finger recess 434. By lifting the lever 430, the bolt 381 is raised 8 via a bar 435 (the same applies to the second bolt 382) and the surgical assistance system 202, 204 can be plugged onto the male interface device 8.

A latching connection is preferably provided between the lever 430 and a segment of the base body 420 underlying it, so that the lever 430 can latch into the base body 420 to fix the coupling between the female interface device 9 of the surgical assistance system 202, 204 and the male interface device 8.

The surgical assistance systems 202, 204 (FIGS. 13 to 15) may be manufactured entirely as single-use products. Instead of the end faces 412, coupling mechanisms for coupling instruments can be directly screwed onto the base body 420, or connected as one piece thereto. The body 420 is preferably formed of an insulating plastic, so that in the case of passive use of an instrument, the surgical assistance system 202, 204 forms an electrical insulation with respect to the male interface device 8 and perhaps the mounting arm 1. In particular, a sterile sheath can be welded to the axial end of the collar 410, or a sterile cover can be welded in, which can be pulled over a part of the mounting arm 1. It is also conceivable that the surgical assistance system 202, 204 is provided in its entirety packaged with a sterile cover. In this way, an user can unpack the surgical assistance system 202, 204 immediately prior to commissioning and said surgical assistance system remains sterile for as long as possible.

FIGS. 16a to 18 show a second embodiment of the male interface device 8 and the corresponding female interface device 9. The same and similar elements are designated by the same reference numerals as in the previous embodiments, so that reference is made in the following fully to the above description. In the following, the differences from the previous embodiments are primarily described.

As can be seen in particular in FIGS. 16a-16d, the first mechanical coupling means 320 comprises a third undercut 500. The third undercut interacts with a third bolt 502 (cf. FIG. 18) which is engageable therein. With reference to a centre plane M (cf. FIG. 16c), the third undercut 500 is disposed substantially between the first undercut 327 and the second undercut 328. A better symmetry in the distribution of forces can be achieved as a result. Towards the axial end face 310, the third undercut 500 comprises a third flank 504, which is oriented to the nose 302 at an angle relative to the central axis L, but substantially perpendicular to the nose surface 303. The third undercut 500 is laterally open in the figures, but may also be closed laterally.

In the direction of the centre plane M, the third undercut 500 is open at the bottom with reference to FIG. 16c, while the first and second undercuts 327, 328 are open at the top. The first and second bolts 381, 382 engage opposite to the third bolt 502 in the corresponding undercuts.

Figure 18:
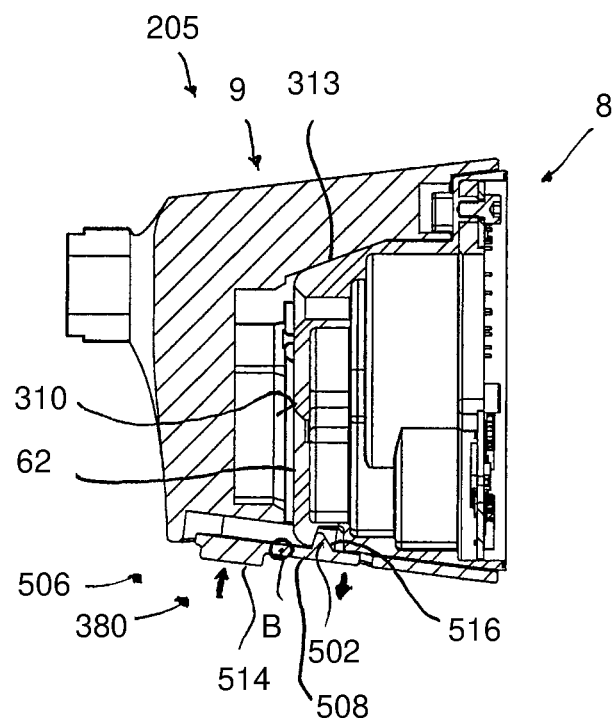
FIG. 18 the surgical assistance system from FIG. 17 in the section A-A.

FIG. 18 now shows the male interface device 8 according to FIGS. 16a to 16d in a female interface device 9 according to the second embodiment implemented in a surgical assistance system 205. The surgical assistance system 205 is passive and has no electronics. It serves, for example, as an adapter for receiving other medical instruments.

The female interface device 9 comprises the third bolt 502, which is disposed in this case pivotable about a bolt pivot axis B. The second mechanical coupling means 380 of the female interface device 9 according to this embodiment comprises only the third bolt 502, and no first and/or second bolts 381, 382. The first and second undercuts 327, 328 are inoperative in this case.

The female interface device 9 accordingly also comprises a second actuating device 506, which is provided to bring the third bolt 502 into a release position. In this embodiment, the second actuating device 506 comprises a rocker 508 which is connected to the body 512 of the surgical assistance system 205 via two film hinges 510, 511. The rocker 508 has a button region 514 which can be pressed, for example, with the thumb. If it is pressed in the direction of the arrow (cf. FIG. 18), the rocker 508 is rotates about the bolt pivot axis B and the third bolt 502 is displaced in the direction of the corresponding arrow in FIG. 18; upon corresponding further rotation, it emerges from the third undercut 500 and releases it.

The film hinges 510, 511 act like springs here, so that the third bolt 502 is pretensioned spring-loaded in the locking position.

The third bolt 502, as has already been described with reference to the first and second bolts 381, 382, is tapered, and comprises an inclined flank 516. In this way, the female interface device 9 can be easily plugged onto the male interface device 8, wherein the third bolt 502 is deflected by the inclined flank 516 in contact with the nose 302, and automatically latches 9 into the third undercut 500 on further pushing the female interface device.

In other embodiments, it may also be provided that the third bolt 502 can be actuated by the (first) actuating device 380. Also, a rotation of the third bolt 502 is not mandatory, and the invention is not limited thereto. Embodiments are also included in which the third bolt 502 is slidable.

The invention claimed is:

1. An interface device configured to couple a surgical assistance system to a mount, the interface device comprising:
   a medical mechatronic male interface device comprising:
      a base comprising an end face and a functional body extending from the end face;
      a first mechanical coupling for positive and/or non-positive coupling to a medical mechatronic female interface device; and
      at least one first electronic interface configured to connect to a second electronic interface of the female interface device,
      wherein the functional body comprises a centring device configured to center the surgical assistance system free of play relative to the base, and
      wherein the centring device comprises a first functional surface, a second functional surface, and a third functional surface that are non-parallel to each other and that have normals which do not lie in a common plane; and
   a medical female interface device configured to be coupled to the male interface device, the female interface device comprising:
      a frame defining a central recess for receiving the functional body of the male interface device; and
      a second mechanical coupling for positive and/or non-positive coupling to the first mechanical coupling of the male interface device,
      wherein the central recess comprises another centring device configured to center the surgical assistance system free of play relative to the base of the male interface device,
      wherein the another centring device comprises a first functional surface, a second functional surface, and a third functional surface for contacting the corresponding first, second and third functional surfaces of the male interface device, and
      wherein the second mechanical coupling comprises at least a first displaceable bolt configured to engage a first undercut of the first mechanical coupling.

2. The interface device according to claim 1, wherein the first displaceable bolt is pretensioned into a locking position.

3. The interface device according to claim 1, wherein the first displaceable bolt is tapered at a free tip.

4. The interface device according to claim 1, wherein the second mechanical coupling further comprises a third displaceable bolt configured to engage a third undercut of the first mechanical coupling.

5. The interface device according to claim 4, wherein the third displaceable bolt is spring-loaded pretensioned, is automatically deflected upon a connection of the female interface device to the male interface device, and latches into the third undercut to counteract a release.

6. The interface device according to claim 4, further comprising an actuating device configured to offset the second mechanical coupling into a release position.

7. The interface device according to claim 6, further comprising a second actuating device configured to offset the third displaceable bolt into a release position independent of the first displaceable bolt.

8. The interface device according to claim 6, wherein the actuating device comprises a lever pivotally supported on the frame and having a gripping segment in contact with the first displaceable bolt on a drive side, wherein the first displaceable bolt is configured to be brought from a locking position into a release position by actuation of the gripping segment.

9. The interface device according to claim 6, wherein the first displaceable bolt is coupled to the actuating device and/or the frame via at least one film hinge.

* * * * *